US012796917B2

(12) United States Patent
Rombach et al.

(10) Patent No.: US 12,796,917 B2
(45) Date of Patent: Nov. 17, 2026

(54) APPARATUS AND METHOD TO SIZE THE ACCOMMODATIVE STRUCTURE OF THE EYE

(71) Applicant: AKKOLENS INTERNATIONAL B.V., Breda (NL)

(72) Inventors: Michiel Christiaan Rombach, Breda (NL); Willem Pieter Van Lawick, Breda (NL)

(73) Assignee: AKKOLENS INTERNATIONAL B.V., Breda (NL)

(*) Notice: Subject to any disclaimer, the term of this patent is extended or adjusted under 35 U.S.C. 154(b) by 695 days.

(21) Appl. No.: 18/010,331

(22) PCT Filed: Jun. 14, 2021

(86) PCT No.: PCT/NL2021/050375
§ 371 (c)(1),
(2) Date: Dec. 14, 2022

(87) PCT Pub. No.: WO2021/256922
PCT Pub. Date: Dec. 23, 2021

(65) Prior Publication Data

US 2023/0277054 A1 Sep. 7, 2023

(30) Foreign Application Priority Data

| | | |
|---|---|---|
| Jun. 15, 2020 | (NL) | 2025833 |
| Jul. 8, 2020 | (NL) | 2026025 |
| Jul. 23, 2020 | (NL) | 2026124 |
| Feb. 19, 2021 | (NL) | 1043948 |

(51) Int. Cl.

| | |
|---|---|
| *A61B 3/117* | (2006.01) |
| *A61B 3/00* | (2006.01) |
| *A61B 3/10* | (2006.01) |
| *A61B 3/107* | (2006.01) |
| *A61B 3/14* | (2006.01) |

(52) U.S. Cl.
CPC ............ *A61B 3/117* (2013.01); *A61B 3/0025* (2013.01); *A61B 3/1005* (2013.01); *A61B 3/107* (2013.01); *A61B 3/14* (2013.01)

(58) Field of Classification Search
CPC ... A61B 3/0008; A61B 3/0025; A61B 3/1005; A61B 3/107; A61B 3/117; A61B 3/14
See application file for complete search history.

(56) References Cited

U.S. PATENT DOCUMENTS

| | | | |
|---|---|---|---|
| 4,993,826 | A | 2/1991 | Yoder, Jr. |
| 2003/0020871 | A1 | 1/2003 | Niven et al. |

(Continued)

FOREIGN PATENT DOCUMENTS

| | | | |
|---|---|---|---|
| CA | 2417776 | C | 6/2012 |
| EP | 1138081 | A1 | 10/2001 |
| WO | 2015003274 | A1 | 1/2015 |

*Primary Examiner* — Jack Dinh
(74) *Attorney, Agent, or Firm* — The Webb Law Firm

(57) ABSTRACT

Apparatus for imaging and measuring the accommodation structure of the eye with the apparatus including a light source providing spot-illumination of the rim of the cornea at a slanted angle with the cornea guiding the light to the largely full rim of the cornea thereby illuminating the rim by scattered light emitted by scattering of light inside the eye at the limbus with the image provided by a telecentric lens which allows for accurate measurements of the diameter of the iris without aid of mechanical calibration tools.

9 Claims, 7 Drawing Sheets

(56) References Cited

U.S. PATENT DOCUMENTS

| | | | |
|---|---|---|---|
| 2013/0093998 A1 | 4/2013 | Bishop |
| 2014/0340635 A1 | 11/2014 | Oyaizu |
| 2019/0290124 A1 | 9/2019 | Laforest et al. |
| 2020/0100671 A1 | 4/2020 | Seitz et al. |

APPARATUS AND METHOD TO SIZE THE ACCOMMODATIVE STRUCTURE OF THE EYE

CROSS-REFERENCE TO RELATED APPLICATIONS

This application is the United States national phase of International Application No. PCT/NL2021/050375 filed Jun. 14, 2021, and claims priority to The Netherlands Patent Application Nos. 2025833 filed Jun. 15, 2020, U.S. Pat. No. 2,026,025 filed Jul. 8, 2020, U.S. Pat. No. 2,026,124 filed Jul. 23, 2020, and U.S. Pat. No. 1,043,948 filed Feb. 19, 2021, the disclosures of which are hereby incorporated by reference in their entirety.

BACKGROUND OF THE INVENTION

Field of the Invention

The present invention relates to intraocular lenses, and in particular, methods and apparatus for sizing certain eye structures.

Discussion of the Related Art

Accurate measurement of the diameter of the sulcus and the ciliary mass of the eye is important for sizing and fitting of intraocular lenses in particular for accommodating intraocular lenses which must accurately fit the anatomy of the eye to function properly, for example, must fit the anatomy of the sulcus and/or the anatomy of the ciliary mass of the eye, in this document collectively and including the iris of the eye, referred to as the accommodation structure. In particular accommodative intraocular lenses, lenses positioned in the accommodative structure which lenses change optical power to allow the eye to focus at different distances, require an accurate fit within components of the accommodative structure, for example the sulcus. The sulcus is the wedge-shaped, space in between the posterior surface of the peripheral section of the iris and the anterior surface of the ciliary mass. So, the sulcus dimensions can be defined by the sulcus-root, the most peripheral rim of the sulcus, the rim at which the iris bends in a posterior direction, with the root having a diameter transversing the eye, and, the sulcus width, which width narrows in lateral direction moving outward from the center of the eye due to the wedging, and, the sulcus-length which is defined by the size of the ciliary mass in the lateral direction. In the present document the term 'sulcus diameter' refers to the distance of the sulcus to sulcus transversing the eye diametrically, meaning transversing the eye through the center of the pupil. In the present document the term 'ciliary mass diameter' refers to the distance of the ciliary mass to ciliary mass transversing the eye diametrically, meaning transversing the eye diametrically eye through the center of the pupil.

The diameter of the sulcus is traditionally established based on, for example, white-to-white measurements indicating the border between the iris and sclera of the eye, by a ruler, tape measure, caliper or any other mechanical tool placed on or near the eye, a simple and inexpensive method. However this method provides an insufficiently accurate estimate for fitting intraocular accommodative lenses because the sizes must be accurate within about 0.1 mm because the accommodative amplitude of the ciliary mass is about 0.4-0.6 mm which implies that a misfit of such lens by a sizing error of, say, >0.1 mm can create refractive errors of the eye. Alternatively, the measurement can be by modern optical coherence tomography, OCT, which provides the required accuracy but which is complex and expensive, and, moreover, a raw digital OCT image requires recalculations by calibration algorithms because of optical distortions of any optical components of the for example, the cornea of the eye.

The sulcus is the space in between the posterior surface of the iris and the anterior surface of the ciliary mass. The sulcus, in particular the peripheral rim of the sulcus, is defined by melanin pigment lining of the iris which layer, at the said peripheral rim, bends in a posterior direction at the sulcus root, after which the pigment layer aligns, and fades, into the sclera of the eye. The pigment layer contains melanocytes which produce melanin which has spectral characteristics. The ciliary mass is defined by a mass of elastic fibrogenic tissues which mass comprises muscular fibers, collectively referred to as ciliary muscle and contains blood to feed the ciliary muscle. The blood, containing haemoglobin, muscle fibers and other components in the eye have all their specific spectral characteristics which characteristics can be accentuated by hyperspectral imaging.

SUMMARY OF THE INVENTION

The apparatus comprises at least one light source, for illuminating the eye, and at least one digital camera, for providing a digital image, and at least one computer, for post-processing the digital image and presenting the digital image on a digital screen and for providing any required digital post-processing of the image.

The light source can generate a single wavelength of light, for example red light which is relatively safe for the eye or can generate specific ranges of wavelengths of light and comprises at least one beam positioning means to position the light beam versus the eye with the means configured to illuminate the interior of the eye, for example, in the preferred embodiment, illuminates the limbus by using the cornea as a waveguide thereby backlighting the accommodation structure, preferably avoiding illuminating the anterior surface of the iris which illumination creates noise which detoriates image resolution. Such back-lighting and imaging of the accommodative structure also prevents the cornea to distort the image and allows calculation of the accommodative structure directly without required correction for corneal image distortions.

Furthermore, the light source can be an adjustable light source, meaning that the shape and/or dimensions of the illumination spot can be adjusted. Such adjustability can be achieved by for example, mechanically, by an sliding adjustable mask and/or a tiltable light source, and/or, alternatively, electro-optically, by, for example, an array of small light sources, for example, at least one array of small RGB LEDs which can be switched on and off in different combinations, or, alternatively, by a liquid crystal arrangement which can provide endless of such shapes and intensities of illumination spots. So, the method can be as follows: firstly, positioning, by tilting and shifting, the illumination spot such the rim of the iris opposite the illumination spot is illuminated meaning that the cornea properly functions as a waveguide, and, secondly: adjust the shape and/or dimensions of the illumination spot to achieve the desired optimum illumination of the sections of the rim to be evaluated. For example, for evaluation of a nasal/temporal section of the iris the light source can be adjusted to (1) maximize illumination both sides of the iris while (2) minimize exposure of these sections by direct illumination, illumination not via the cornea) which can be achieved by, for example, clipping the tips of the illumination spot to reduce such direct illumination.

The beam shape projected by the beam positioning means can be a slit-configuration, as in the traditional ophthalmology slit lamp, to provide an elongated slit shaped light beam to be projected on the sclera, or, alternatively, the beam can have, for example, an partly annular shape, a semilunar shape or a sickle shape. The beam positioning means can projects at least one such spot-shape with the shape of the light beam is not restricted to said shapes.

The retina can be protected from excessive light intensities by, for example, a circular light shield casting a central shadow covering the pupil of the eye or, alternatively, by a contact lens with a central opaque section. All illumination can be continuous or in a flash arrangement and any of the beam positioning means can also be, for example, in a partly ringlight configuration fitted around the camera lens.

In the preferred embodiment the light source can provide at least one light beam with the beam comprising at least one range of wavelengths with the range coinciding with at least one absorption spectrum of the ciliary mass which contains said heamoglobin, so with the range, for heamoglobin, preferably including wavelengths within the range of, for example, 400 and 699 nm. Note that other absorption spectra can be included. Alternatively, the light source provides at least one light beam with the beam comprising at least one range of wavelengths with the range coinciding with at least one absorption spectrum of the of the sulcus with the lining of the sulcus comprising melanin, so the wavelengths preferably include wavelengths below 400 nm and above 699 nm but not restricted hereto.

To generate said ranges of wavelengths of light the light source can comprise a combination of at least one broadband light source and at least one fixed wavelength filter, for example, a traditional camera colour filter which filter can be exchanged for another colour filter to generate another range of wavelenghths, or, alternatively, multiple filters can be applied for combination of different ranges of wavelengths in a single image. Note that a light filtering fluid in the tear film, for example, a standard ophthalmological compound such as fluorescein, or, alternatively, a coloured, contact lens, for example a scleral contact lens, is regarded as a fixed wavelength filter in the context of the present document.

Alternatively, to generate said ranges of wavelengths of light, the light source can comprise at least one dedicated light element, such as a RGB-LED, a NEO-LED or a laser. The apparatus can include an illumination combination with at least one light emitting diode, LED, or laser, or, alternatively, an array of LEDs/lasers to provide a broad band light source which band can be narrowed by switching off selected coloured LEDs/lasers. For example, a deep-red array of LEDs/lasers to accentuate the sulcus spectrum in combination with any yellow, blue, and/or green LED/lasers to accentuate the ciliary mass, or any other combination for optimum accentuation. Alternatively, the light source can comprise a combination of at least one broadband light source and at least one tuneable wavelength filter, for example a liquid crystal tuneable filter.

The apparatus can comprise a tuneable filter, for example an acousto-optic tuneable filter, or, alternatively, an angle-dependent tuneable filter, or alternatively, a liquid crystal tuneable filter which is electronically controlled and selects a target wavelength or range of wavelengths which selection can be at speeds up to 1 kHz. Such apparatus can provide by scanning the ciliary sulcus structure with light wavelengths within at least one relatively narrow band which band can be centered around at least one spectral peak of the ciliary mass, or, alternatively, centered around at least one peak of the sulcus lining, or, alternatively, centered around a combination of at least one spectral peak of the ciliary mass and at least one spectral peak of the sulcus lining. Scanning also provides hitting the precise peaks of the ciliary mass and the sulcus lining. These peaks are individually shifted because of the spectral effects of the individual sclera and other tissues of the individual eye. Scanning over a, generally narrow, range of wavelengths will allow selection of such individual peaks.

Alternatively, the light source provides at least one light beam including a combination of at least two ranges of wavelengths with the combination including at least one the range coinciding with the absorption spectrum of haemoglobin and at least one range coinciding with the absorption spectrum of melanin.

Furthermore, the apparatus can also include at least one light polarizing filter, or, alternatively, can comprise at least two polarizing filters in a cross-polarizing arrangement with at least one filter positioned in the incoming light beam, being the beam emitted by the light source and at least one filter positioned in the outgoing light beam, being the beam emitted by the eye. Such polarization can provide absorption of light reflected by tear film and/or corneal surfaces, or, alternatively, at least two polarizing filters can provide cross-polarization for further accentuation of accommodative structures which is a procedure well known for removing 'noise', meaning removing non-informational, light signals.

Alternatively, the light source can comprise a broadband light source only with the source comprising no filtering components, for example, as a white light source. A digital camera comprising a colour sensor, for example a sensor fitted with a standard Bayer filter, and with the computer providing, in post-processing, a digital filtration of wavelengths on the, colour, digital image and, alternatively provide for post-processing digital scanning, a digital scanning through narrow bands of wavelengths present in the range of the white light and/or light in the infrared and/or ultraviolet light wavelength ranges.

The camera can include a focusing optical arrangement, for example and generally, a standard macro-camera lens, providing at least one image of the ciliary sulcus structure onto a digital optical sensor to provide translation of the image in a digital image. The macro-camera lens is preferably a lens of a relatively long focal distance to maximize flattening of the image by minimizing aspherical distortions which distortions can affect the accuracy of establishing any size of the accommodative structure during analysis of the images. The camera can also be an ophthalmology slit-lamp camera, or, alternatively, any technical camera, or, alternatively, even be a smartphone camera comprising a sensor with a sufficiently resolving sensor and with the lens fitted with an appropriate macro-lens. Furthermore, the camera can be an infrared camera, for example a camera from which the Bayer filter is removed from the camera sensor which sensitizes the camera sensor to infrared light which is a procedure which can, as the inventors can testify to, void guarantee of the camera. Furthermore, the camera can be fitted with a telecentric optical lens which projects an image on the digital sensor with the size of the image being, within a range of distance and sharpness of the image, independent of the distance of the lens objective to the object, the eye so that the use of external calibration aids is not required. So, the telecentric lens, as used in the present apparatus has its entrance or exit pupil at infinity an orthographic view of the eye so that oblique rays pass through the center of the aperture stop parallel to the optical axis in front of or behind the system which makes object-space telecentric. The image magnification is independent of the eye's distance or position in the field of view, provide the same magnification at al range of distances even if the eye is too close or too far from the lens may still be out of focus with the blurry image will have the same size as the correctly focused image would. The telecentric lens of the preferred embodiment of the apparatus provides a usable image over a range of about 2 cm which range covers the distance of almost all eye of all patients on the headstand. Slight image blur can be corrected by adjustment of focus the image prior to image acquisition or can generally be corrected for during image digital post processing.

The computer provides post-processing the digital image and presenting the digital image on a digital screen and the computer can provide any digital processing of the image, for example, increase resolution of the image, or, alternatively, increase contrast of the image, or, alternatively, any combination of increase of resolution and increase of contrast of the image, all provided in coloured images or, alternatively, in black and white images, as in IR-images. The digital manipulation can include, for example, also contour attenuation by digital Laplace filtering, and/or interpolation, and/or addition of noise to increase colour depth, followed by digital wavelength selection, pixel-by pixel, if required, for example, based on histograms. Furthermore, as mentioned, the apparatus can include a light source which provides only at least one broadband light source, for example broadband white light, and computer algorithms to provide image post-processing digital filtration for various ranges of wavelengths, separation of colours.

The accommodative structure can also be scanned, for example, over time or scanned simultaneously, by a light beam comprising light of wavelengths of, for example, 200 nm to >1000 nm, within the range of visible light or outside this range, to image the ciliary mass and the sulcus lining and/or any other structures and tissues, or, alternatively, scanned by any multiple ranges of wavelengths. The accommodative structure can be scanned, subsequently, or, alternatively, simultaneously, by a light beam comprising a range within the red-infrared, RIR, spectral spectrum because melanin effectively absorbs red-infrared, RIR, wavelengths. Or, alternatively, the accommodative structure can be scanned at a number of ranges of wavelength in order to select the best image post-scanning and post-processing digital reconstruction including merging of images, overlay images, taken at different ranges of wavelengths. Scans can be if course also be carried out in shorter wavelengths as far-blue and ultra-violet, UV, ranges. However, for such shorter higher energy wavelengths the amplitude of light and exposure times must be carefully monitored to protect the retina of the eye.

The method for imaging the accommodation structure of the eye can include the use of external calibration marks to support calculation of desired diameters of anatomical or other structures, with the structure being, for example, the ciliary mass and the sulcus of the eye, can comprise the following steps, not necessarily in such said order, of (a) Adding at least one calibration mark to the eye. The calibration mark can be provided by at least one calibration means on the eye with the calibration mark providing the base for establishing of dimensions and sizes of any component of the accommodative structure, for example the ciliary mass and/or the sulcus. The calibration means can be a physical mark surgically deposited into the eye, for example, at least one, traditional, surgical gentian violet fluid mark of precise dimensions deposited by surgical needle, for example, two dots at a precisely measured distance in the sclera of the eye. Alternatively, the calibration means can be an eye-covering component comprising the physical mark, for example, a mark onto an eye-covering component such as a, for example, scleral, contact lens. Alternatively, the eye-covering component can comprises at least one calibration bar to be included in at least one of the images which can be a small calibration bar or disc of precisely known size, for example, a black, strip of contact lens material which floats on the sclera in the tear film close to the ciliary sulcus structure or, alternatively, the calibration bar is a hand-held calibration bar with such a strip, of any size or shape of known dimensions, mounted, by, for example, sticky tape, on a hand-holder, for example, an extended paperclip to be manipulated, to be positioned on the eye, by the operator, for example onto the sclera adjacent to the rim of the iris as close as possible to the accommodative structure, which procedure involving a paperclip was performed, say, 'uncoordinated', by the first author of his document on his own right eye resulting in an unfortunate accident which required medical attention, and, (b) illuminating the eye through the cornea as a waveguide or through the sclera of the eye by the beam positioning means, thereby backlighting the accommodation structure of the eye and preferably avoiding illuminating the anterior surface of the iris, and, (c) imaging, by a digital camera, the accommodation structure of the eye and processing at least one digital image, and, (d) post-processing the at least one digital image, for instance to increase contrast and/or resolution of the digital image and presenting the processed digital image on a digital screen, and, (e) identifying at least one structural marker, such as the ciliary mass or the lining of sulcus of the eye, and, (f) comparing, post-processing, the size of the calibration mark to the size the structural marker to establish the size of the structural marker, and, (g) any combination of the steps listed above can, but not necessarily has to, be automated by computer algorithms.

DESCRIPTION OF THE INVENTION

Figure 1:
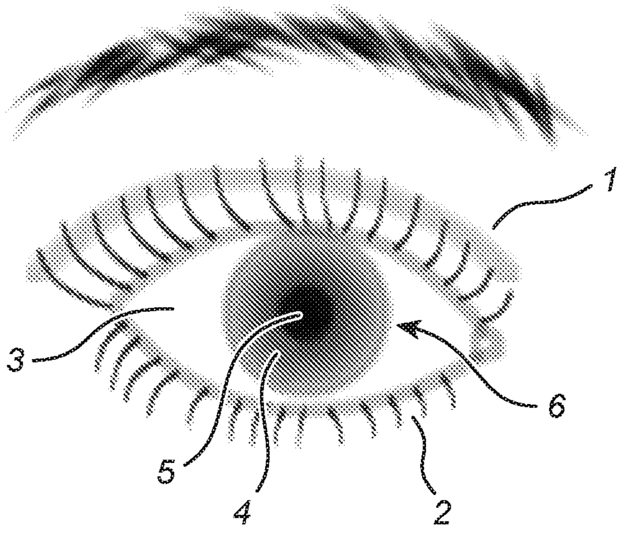
FIG. 1 shows a frontal view of the human eye with the eyelids, 1, 2, the sclera, 3, the iris, 4, the pupil, 5 and the location, 6, under the iris, of the accommodative structure.
Figure 2:
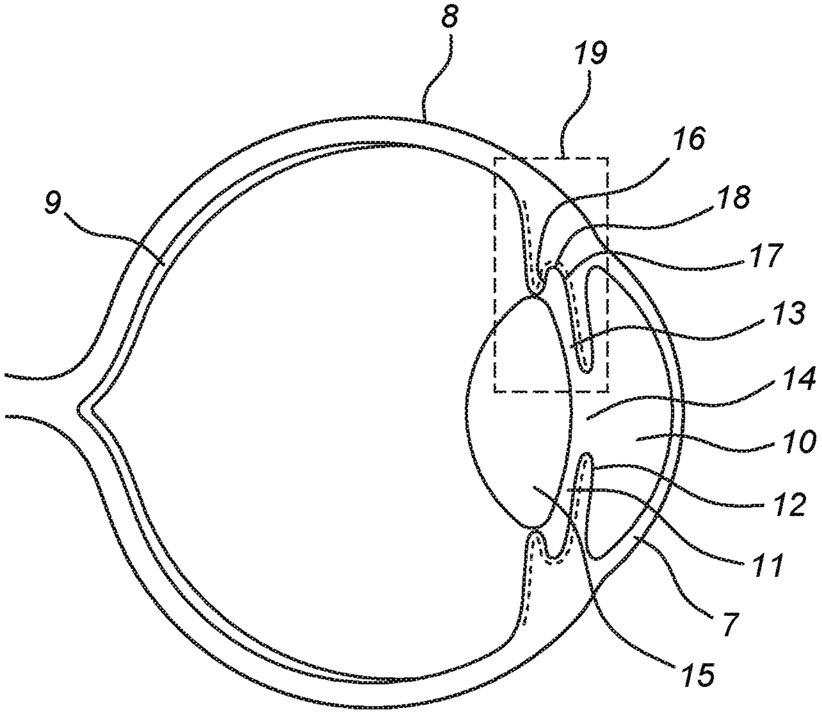
FIG. 2 shows a schematic cross-cut of the human eye with the cornea, 7, the sclera, 8, the retina, 9, the anterior chamber, 10, and the posterior chamber, 11, the iris, 12, the melanin pigment lining of the iris, 13, the pupil, 14, the lens, 15, the ciliary mass, 16, the sulcus, 17, with the sulcus-root, 18, and, the marked area, the accommodative structure, 19.
Figure 3:
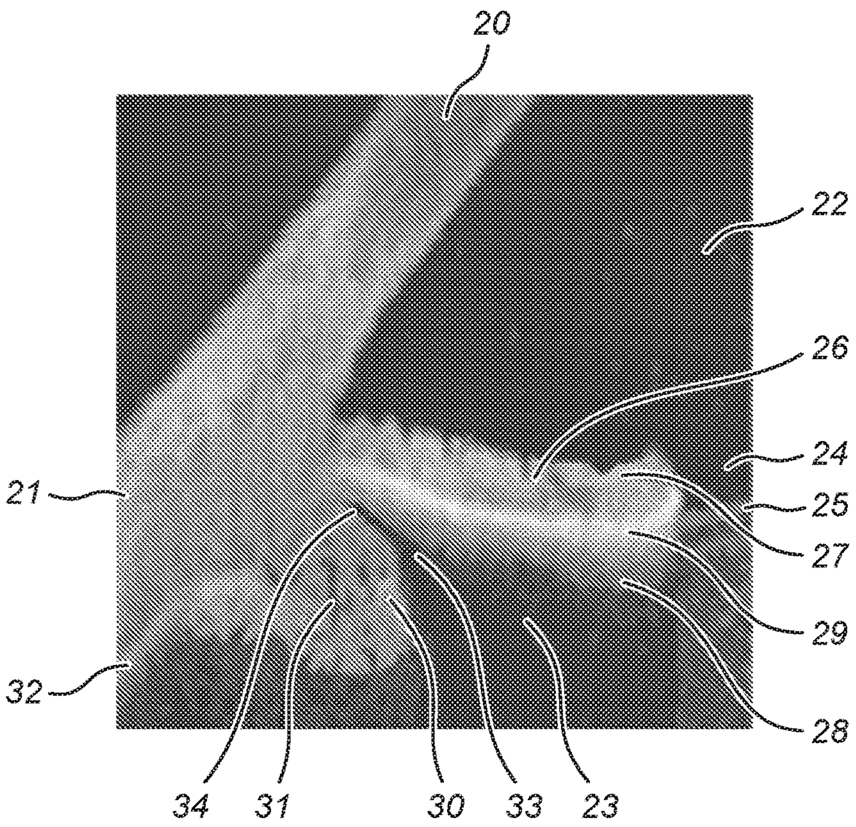

FIG. 3 shows an OCT image, a cross-cut, of the accommodative structure with the cornea, 20, the sclera, 21, the anterior chamber, 22, the posterior chamber, 23, the pupil, 24, the lens, 25, the iris, 26, with the anterior surface of the iris, 27, and the posterior surface of the iris, 28, the main melanin pigment lining of the iris, 29, which continues, 30, over the ciliary mass, 31, and thereafter, at the inner lining of the sclera, fades, 32, and, the sulcus, 33, with the sulcus-root, 34. In this Figure, the ciliary mass and the sulcus are digitally accentuated for illustrative purposes.

Figure 4:
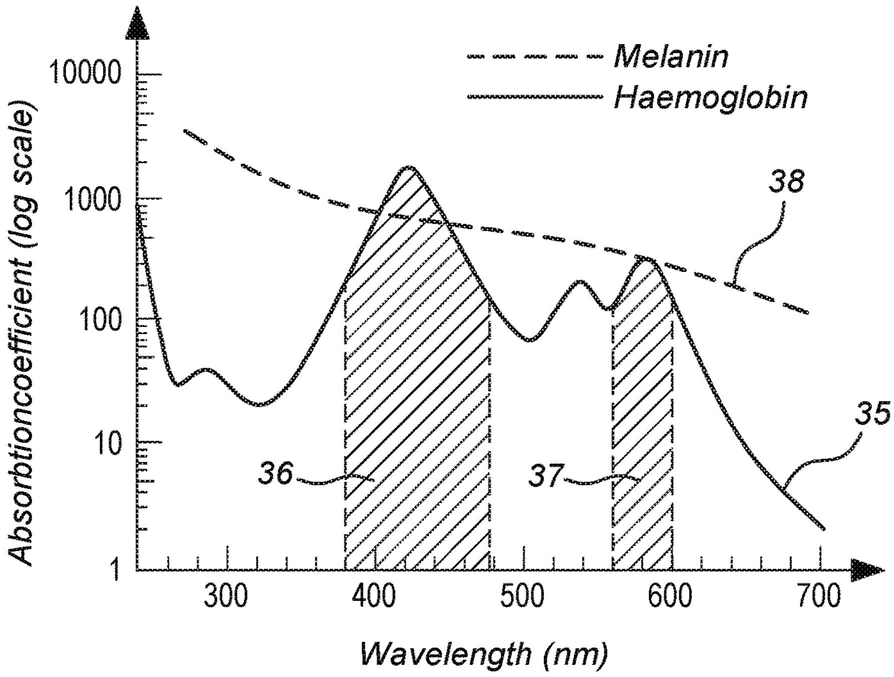

FIG. 4 shows the absorption spectrum of haemoglobin, 35, with desired ranges of wavelengths, 36, 37, but not necessarily limited to these ranges, to accentuate the ciliary mass and the absorption spectrum of melanin, 38 to accentuate the lining of the sulcus, preferably the lining of the sulcus-root.

Figure 5:
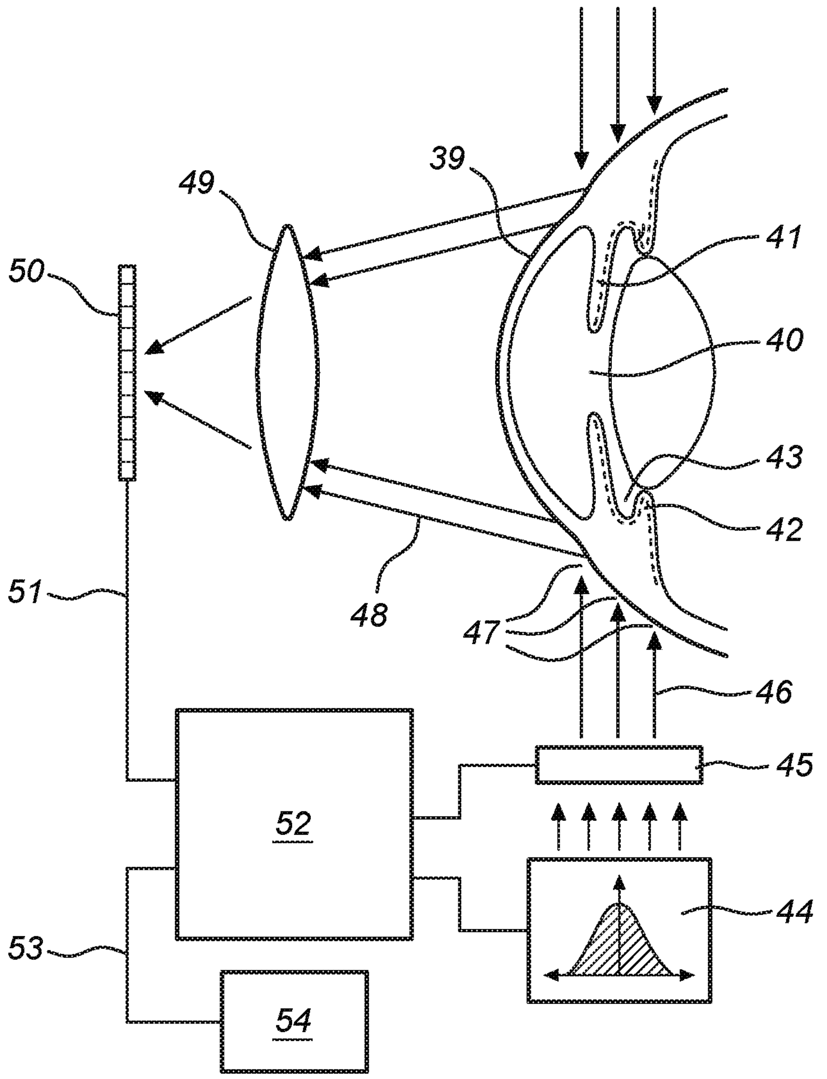

FIG. 5 shows a schematic representation of the preferred embodiment of the apparatus to measure dimensions of the accommodative structure of the eye, in particular the ciliary diameter, the distance from the ciliary mass to ciliary mass, transversing the eye, and the sulcus diameter, the distance from root to root, transversing the eye. The light source of this embodiment provides at least one beam of selected ranges of wavelengths to be projected onto the sclera with the schematic showing the eye with the cornea, 39, the pupil, 40, the iris, 41, and the accommodative structure including the ciliary mass, 42, and the sulcus, 43, with the apparatus, in this preferred embodiment, comprising a broadband light source, 44, with, in this example, a wavelength filter and a beam positioning means, 45, providing an incoming light beam of selected wavelengths, 46, directed towards the sclera at the location, 47, of the accommodative structure at, this example, an angle parallel to the iris plane with the outgoing light beams, 48, focused by a focusing optical arrangement, 49, onto a digital sensor, 50, which is coupled, 51, to a computer, 52, which computer provides both digital enhancement of the image and which is coupled, 53, to a digital display or screen, 54.

Figure 6:
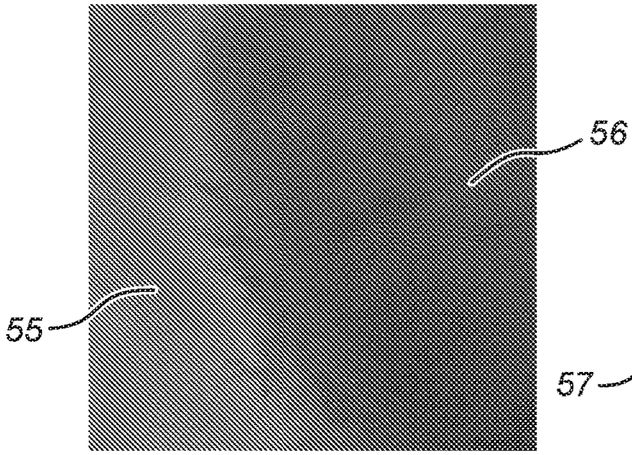

FIG. 6 (with FIG. 7) shows, as an example, a pre-processed digital image of a section of the accommodative structure. Details of the accommodative structure are not visible except for the sclera, 55, and the iris, 56 and details of the accommodative structure cannot be measured with sufficient accuracy.

Figure 7:
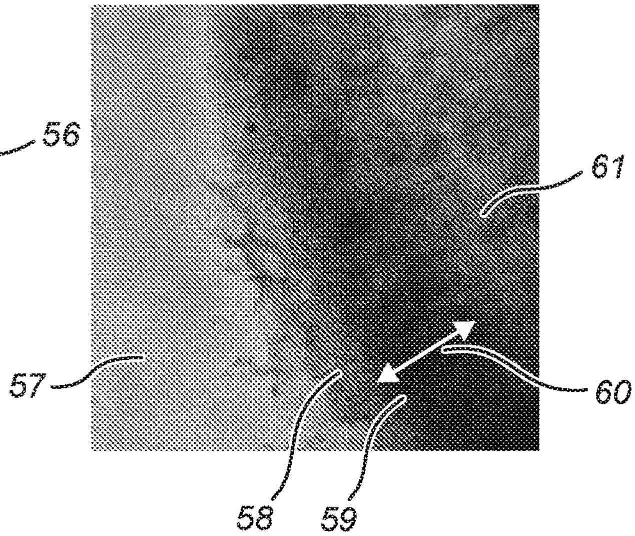

FIG. 7 (with FIG. 6) shows the post-processed digital image, by proprietary digital imaging algorithms, of the same section of the accommodative structure with the sclera, 57, the limbus of the eye, 58, sulcus root, 59, and a dark grey/blackish band representing the ciliary mass, 60 and the central section of the iris, 61. Details of the accommodative structure are clearly visible and can therefore be measured with sufficient accuracy. In such final digitalized and digitally enhanced image the combination of the sulcus are and the ciliary mass are projected onto the iris and represented by a band of dark grey to black because the back-light is blocked by the, weak, posterior melanin lining of the ciliary mass followed by the, weak, anterior melanin lining of the ciliary mass followed by blockage by the melanin in the iris, a total of three to four light blocking layers. More centrally the back-light is filtered only by iris and thus shows up in the image as a lighter shade of grey.

Note that an image illuminated and acquired along the direction of the optical axis will provide an image with only a single grey band provided by blockage of back-light by a combination of the ciliary mass and the iris. Images at other angles allow for separation of the ciliary mass and the iris which separation can also be further increased by multiple imaging with separate wavelengths as set forth elsewhere in this document.

Figure 8:
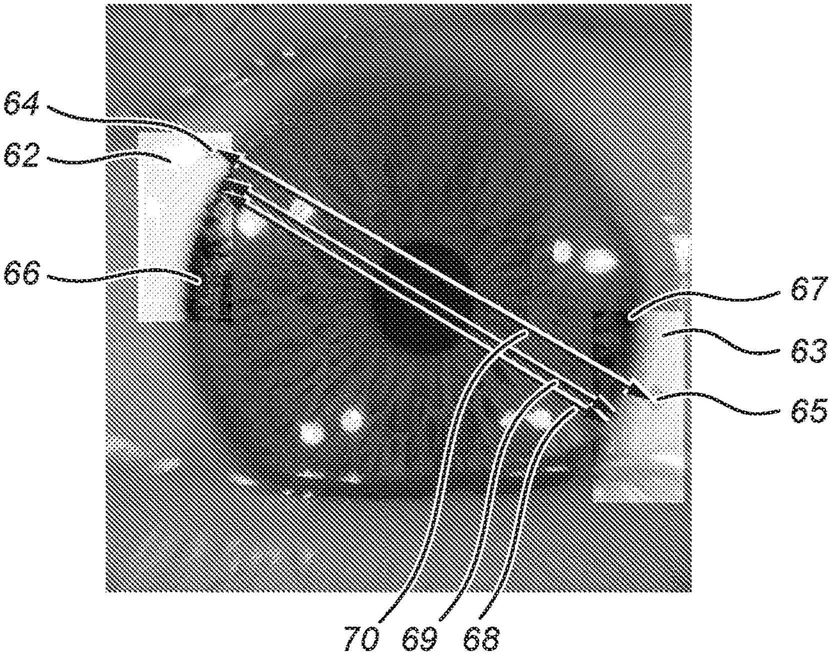
Figure 9:
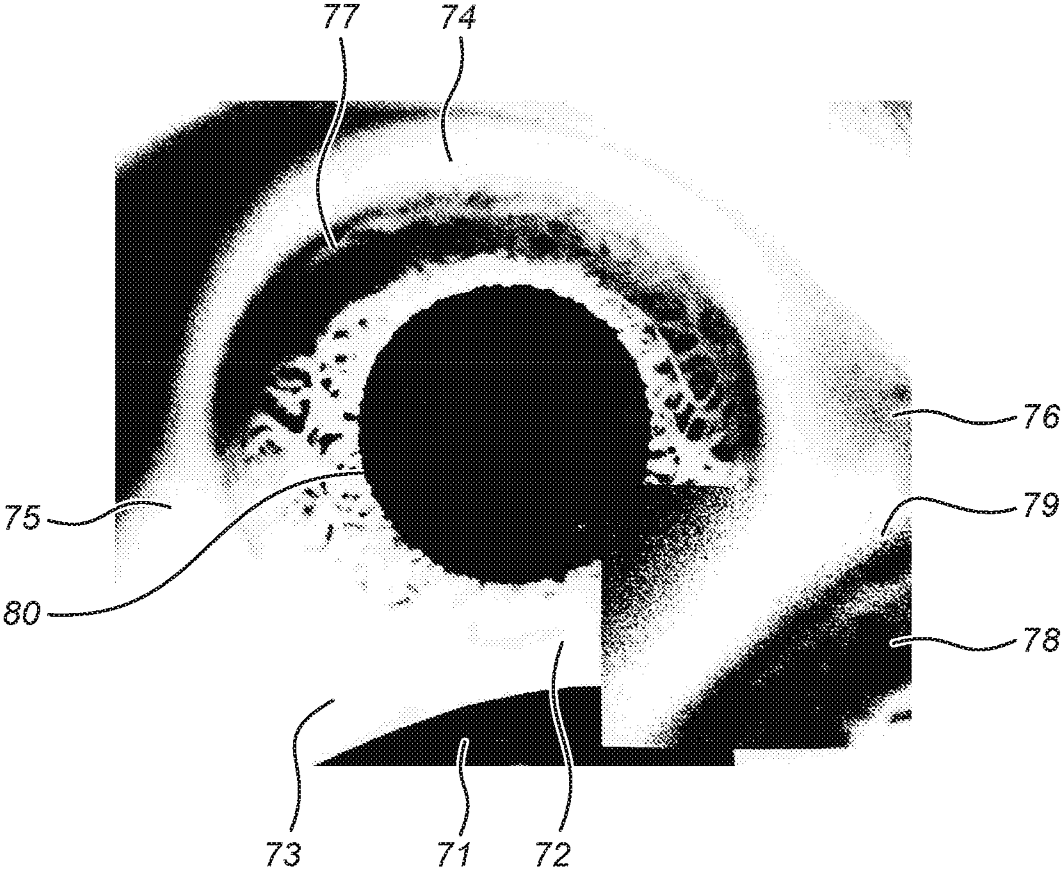

FIG. 8 shows a final image with a standard slitlamp image of the eye taken with frontal illumination. From this image the diameter of ciliary mass and sulcus root can be accurately determined. The image shows, in two diametrically opposed insets, 62, 63, the, in this example corneal, marks for calibration, 64, 65, and the digitally enhanced accommodative structure (see also FIGS. 6-7). The image shows the dark grey banding, 66, 67, the diameter of the ciliary mass, 68, the diameter of the sulcus, 69, and the distance between the markers, 70. The diameters of the ciliary mass and the sulcus-root can be established based on the prior known distance between the, in this example, corneal markers. However, accuracy of measurements is significantly improved by the novel illumination methods as set forth in this document. Note that in standard slitlamp images, frontal illumination, the fat-rich arcus senilis can significantly blur the image which blurring only be partly remedied by using shorter, blueish, frequencies of illumination FIG. 9 shows an image of the eye of which the rim of the cornea is illuminated, in this example by red light (650 nm), by a single light source, 71, with a semilunar spot, 72, in a vertical direction from the inferior side of the eye, 73, with the light traveling via the cornea to the superior side of the eye, 74, as well as, by horizontal spreading, to both sides, 75, 76, of the eye, while illumination of the iris, 77, is largely prevented. This image was digitally processed, mainly increase of contrast and adjustment of pixel-depth to accentuate the rim of the pigment layer. The inset, 78, lower right, shows the distinct border of the pigment rim, 79, which can be digitally determined within a 0.1 mm accuracy. Note the wide pupil, 80, which shows that only minimal amount of light enters the pupil so that the method ensures that the pigment diameter and thus sulcus diameter is measured at maximum diameter with minimal contraction. Note also that with such embodiment a single light source is used to obtained an image of both sides of the iris in a single image.

Figure 10:
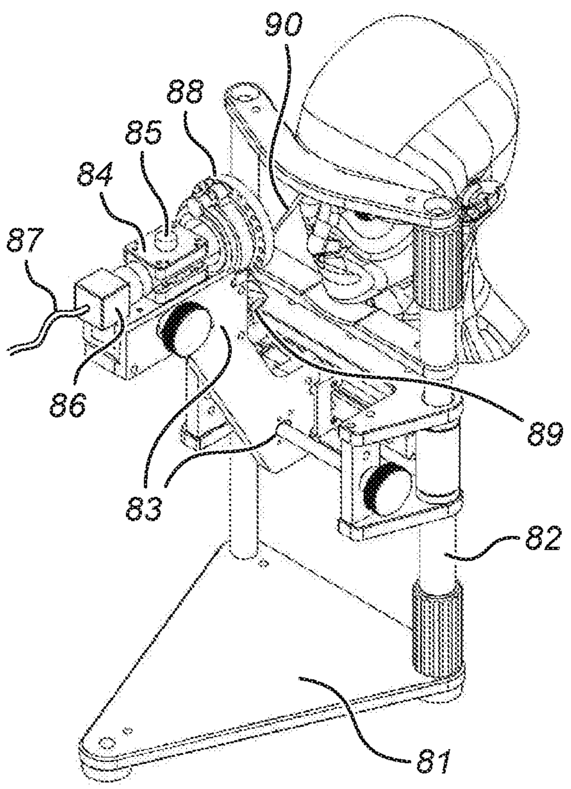

FIG. 10 (with FIG. 11) shows the preferred embodiment of the apparatus with a footstand, 81, and an adjustable headstand, 82, as well as the camera and light source attachment, 83, with various adjustment knobs. The telecentric lens, 84, is fitted with target light, 85, which, via a prism, projects a small target light spot for the eye to center upon, a digital camera, 86, fitted with a connection cord, 87, for electric power and data transmission. The lens is also fitted with a ringlight, 88, producing diffuse lighting for taking general overview images of the eye, as in a standard slitlamp, which images can be illuminated by white light or by light of any wavelength or combination of wavelengths. The light source, 89, providing the illumination beam, 90, for the illumination spot to illuminate the rim of the cornea is fitted onto a rotational swiveling arm (see also FIG. 11), rotating in the plane perpendicular to the optical axis, so that images can be obtained at different illumination angles.

Figure 11:
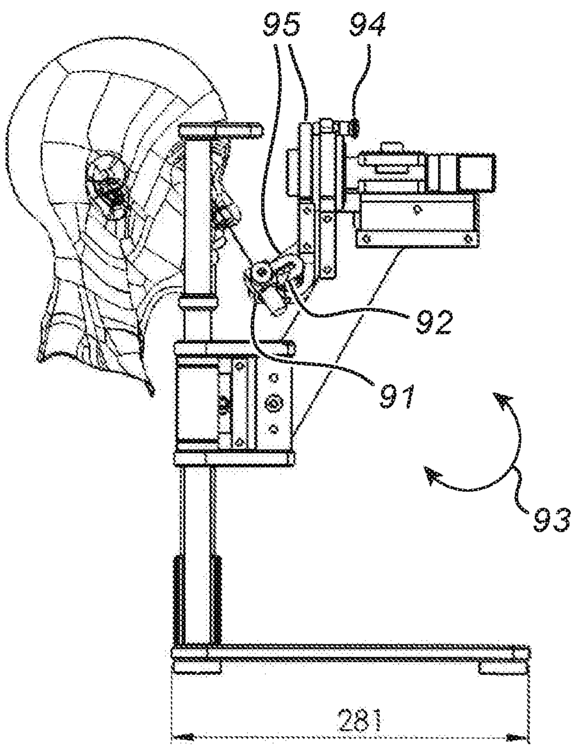

FIG. 11 (with FIG. 10) shows a side view of the preferred embodiment, with the light source for the light spot, 91, is fitted onto a swiveling arm, 92, swiveling in a direction along the optical axis, as indicated by the arrow, 93, which allows the operator to position the illumination spot precisely at an angle for maximum uptake, meaning the best angle for wave guiding, of light by the cornea. A stopper knob, 94, fixates the rotational swiveling arm, 95, in a desired position which arm rotates the light source in the plane perpendicular to the optical axis.

Figure 12:
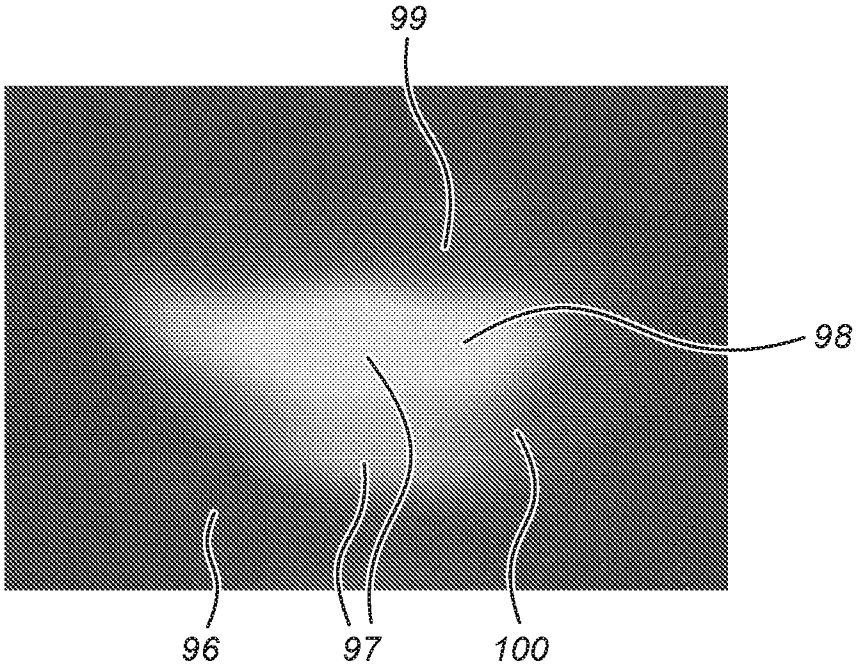

FIG. 12 (with FIG. 13) shows an example of, in this example, the sclera of the eye, 96, (weakly illuminated) and, in this example, a semilunar illumination spot, 97, (strongly illuminated) illuminating the rim or the cornea a slanted angle with the spot provided by a single light source, for example, one LED, one NEO-LED or one laser fitted with, for example, a shaped optical mask, projecting the light beam onto the inferior section of the rim of the cornea. In this example the spot is projected on the lab bench onto an artificial eye to show the central semilunar shaped illumination spot, 98 and the fading crescent, 99, of light rays inside the cornea and the fading crescent, 100, at the inferior section of the spot is light scattered by the sclera of the eye. Such standard spot size and shape mostly generally functions well but different sizes and/or different shapes of spots can be applied by mask attachments to the light source, for particular eyes. The masks can also comprise a polarizing filter for cross-polarization with the complementary polarizer fitted onto, for example, the objective of the telecentric lens.

Figure 13:
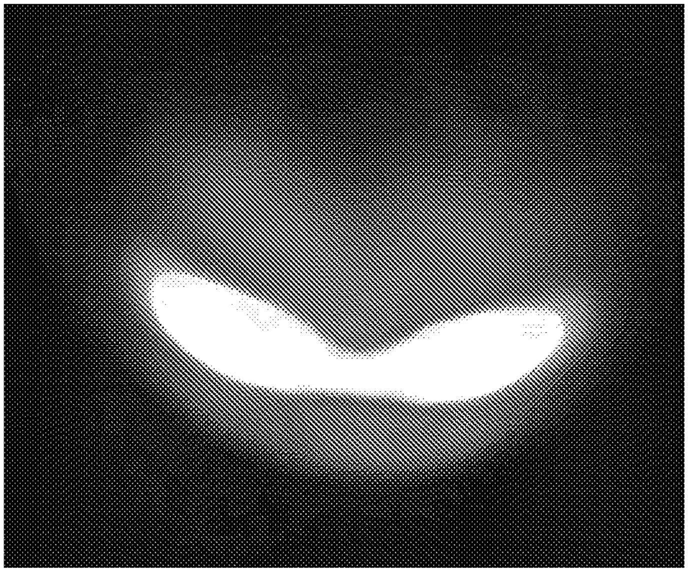

FIG. 13 (with FIG. 12 to which Figure is referred for details) shows, in this example, a sickle-shaped illumination spot with a reduced amplitude of light in the central section resulting in accentuating the temporal and nasal sections of the iris rim and thus prevents overexposure of the superior section of the rim of the cornea to which, in general, most of the illumination will be directed. Note that different eyes might require a different shape of spot. Such different shapes can be provided by, for example, inverting the spot, turning the spot upside-down, and/or changing the spot shape and/or the spot size and/or adjusting the amplitude of illumination. The preferred embodiment of the apparatus can come with a number easy to fit masks or such masks will be fitted to the light source in, for example, a revolver type adjustment construction. Note also that an astigmatic cornea will distribute the illumination of the rim of the cornea unevenly which can generally easily be corrected by minor rotation of the light source and/or mask in the plane perpendicular to the optical axis.

Figure 14:
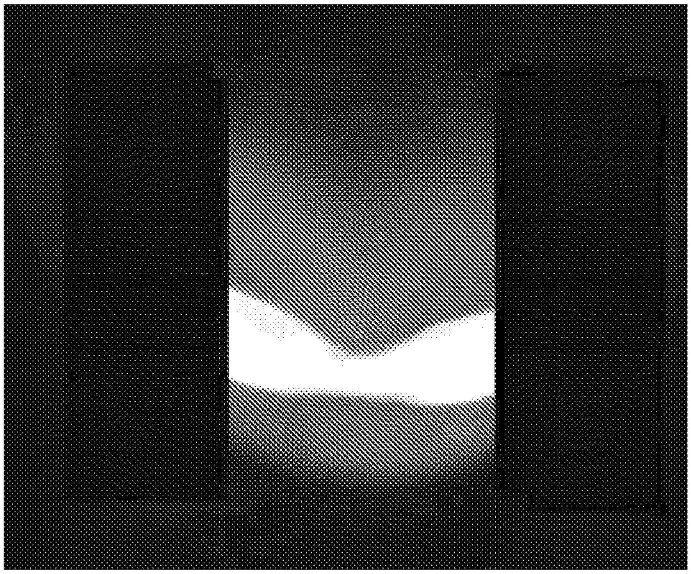

FIG. 14 (with FIGS. 12-13) shows the same illumination spot as in FIG. 13, but with a, in this example, digitally, for illustrative purposes, clipped illumination spot which spot can be clipped adjustable as to adjust for maximum illumination by light guided through the cornea of desired sectors of the rim of, for example, the iris while minimizing direct illumination of these sectors by the light source which direct illumination causes loss of contrast and thus inferior images. The light source can include, for example, a wedge shaped shiftable mask to achieve such clipping.

Figure 15:

FIG. 15 (with FIGS. 12, 14 to which Figures is referred for details) shows, in this example, a sickle-shaped illumination spot with a greatly reduced amplitude of light in the central section resulting in further accentuating the temporal and nasal sections of the iris rim. Such spot shape can be projected, as in this case, with a centrally closed optical mask. Such spot shape can also be projected by, albeit more technically complex, by a double light source which method is considered to be disclosed and part of the present document.

So, in summary, this invention discloses an apparatus for imaging the accommodation structure of the eye, the accommodative structure including the ciliary mass and the sulcus of the eye, with the apparatus comprising at least one light source, for illuminating the eye, with the light source comprises at least one beam positioning means configured to illuminate the interior of the eye by backlighting the accommodation structure, preferably avoiding any illuminating of the anterior surface of the iris, with the main direction of illumination differing from the direction of the optical axis of the eye, and, at least one digital camera, for providing a digital image with the camera arranged to provide an image of the eye with the image including the accommodation structure, and, at least one computer, for post-processing by, for example, merging multiple images and/or processing the digital image by image-enhancing software followed by presenting the digital image on a digital screen.

The light source can provide at least one light beam with the beam comprising at least one range of wavelengths with the range coinciding with at least one absorption spectrum of the ciliary mass which contains heamoglobin, so with the range preferably including wavelengths within the range of 400 and 699 nm. Alternatively, the light source can provide at least one light beam with the beam comprising at least one range of wavelengths with the range coinciding with at least one absorption spectrum of the of the sulcus with the lining of the sulcus comprising melanin, so the wavelengths preferably including wavelengths below 400 nm and above 699 nm. Alternatively, the light source can provide at least one light beam including a combination of at least two ranges of wavelengths with the combination including at least one the range coinciding with the absorption spectrum of haemoglobin and at least one range coinciding with the absorption spectrum of melanin.

The light source can comprise a combination of at least one broadband light source and at least one fixed wavelength filter, or, alternatively, the light source can comprise at least one dedicated light element, such as a LED or a laser, or, alternatively, the light source can comprise a combination of at least one broadband light source and at least one tuneable wavelength filter. Furthermore, the apparatus can include at least one light polarizing filter which filter can be positioned in the incoming light beam, in between the light source and the eye, or, alternatively, the filter can be positioned in the outgoing light beam, in between the eye and the camera. Also, the apparatus can includes at least two polarizing filters, preferably linear polarizing filters, arranged in a cross-polarizing arrangement with at least one polarizing filter positioned in the incoming light beam, in between the light source and the eye and with at least one polarizing filter be positioned in the outgoing light beam, in between the eye and the camera.

Note that the image is optically distorted in frontal imaging of the eye, especially distortion of the width of greyish bands in the final digital image because of the, spherical, bending backward of the sclera. Such distortion can be corrected by (a) the optical arrangement on the camera, by, for example, use of, traditional, spherical corrected printing objectives or, alternatively and preferably, (b) be corrected during digital post-processing of the image, by, 'digitally-flatten' the image based on the spherical bending parameters of the particular eye, or, alternatively, 'digitally-flatten' the image based on the spherical bending parameters of the average eye, or, alternatively, (c) apply a correction factor to the said distorted measurements.

The method for imaging the accommodation structure of the eye, with the structure being the ciliary mass and the sulcus of the eye, with the method comprising the steps of (a) adding at least one calibration mark to the eye, and, (b) illuminating the eye through the sclera of the eye, thereby backlighting the accommodation structure of the eye and preferably avoiding illuminating the anterior surface of the iris; golflengtes, and, (c) imaging, by a digital camera, the accommodation structure of the eye and processing at least one digital image, and, (d) post-processing the at least one digital image, for instance to increase contrast and/or resolution of the digital image and presenting the processed digital image on a digital screen, and, (e) identifying at least one structural marker, such as the ciliary mass or the lining of sulcus of the eye, and, (f) comparing, post-processing, the size of the calibration mark to the size the structural marker to establish the size of the structural marker, and, (g) the method can also comprise any digital image-enhancing software processing to merge multiple images and to increase resolution and/or contrast of the image. So, the method also comprises any digital merging of multiple images and processing by digital image-enhancing processing to increase resolution and/or contrast of the accommodative structure.

Largely frontal illumination in combination with frontal imaging can provide, in some cases, satisfactory images especially with eyes with low iris pigmentation, meaning light blue eyes. So, the method can also comprise illuminating the eye by a wide range broadband white light at any angle with the computer providing post-processing digital for selection of at least one range of wavelength and processing by digital image-enhancing processing to increase resolution and/or contrast of the accommodative structure, or, alternatively, the method comprises illuminating the eye at any angle by at least one light beam including a combination of at least two ranges of wavelengths and with the computer providing processing by digital image-enhancing processing to increase resolution and/or contrast of the accommodative structure.

Furthermore, the method can include illuminating the eye by a wide range broadband of only white light with the computer providing post-processing digital for selection of at least one range of wavelength which broadband can include at least one range of infrared light and/or ultraviolet wavelength light. The method can also include positioning of at least one light polarizing filter positioned in the ingoing light beam, in between the light source and the eye or in the outgoing light beam, in between the eye and the camera, or, alternatively, the method can include positioning of at least two light polarizing filters in a cross-polarizing arrangement with at least one filter positioned in the incoming light beam, in between the light source and the eye and at least one filter in the outgoing light beam, in between the eye and the camera. Any such application of polarized light can reduce undesired light noise which noise can degrade the digital image by, mainly, reduction of contrast in the image.

Furthermore, the sclera, and thus the sulcus root, also slightly, say, a 0.05 to 0.1 mm, changes its in diameter during accommodation. So, the method can include treatment of the eye, prior to the measurements, treatment of the eye with any cycloplegia pharmaceutical to widen and stabilize the diameter of the ciliary mass, or, alternatively, treatment with a pilocarpin pharmaceutical to narrow and stabilize the diameter of the ciliary mass. Also, the eye can, prior to the measurements, subsequently be treated with a cycloplegia pharmaceutical and a pilocarpin pharmaceutical, or a treatment vice versa, to provide multiple images to establish multiple diameters of the ciliary mass and/or sulcus root. Or, alternatively, the eye can be kept in the dark for, say, a few seconds, following positioning the light source and before capture of the image to allow the iris to relax to a maximum diameter, so the image is taken in the dark by flash illumination by the light source. Such procedure can, for example, provide information on the accommodative status of the accommodative structure.

So, in summary,. The present document discloses an apparatus for imaging and measuring the accommodation structure of the eye, which structure includes, but is not restricted to, the ciliary mass, the iris and the sulcus. The apparatus can comprise at least one light source for illuminating the eye, and, at least one digital multichrome or monochrome digital camera comprising at least one optical lens for providing at least one digital image with the camera with the camera coupled to at least one computer for post-processing the digital image and presenting the digital image on a digital screen followed by storage of the image for post processing and further analysis.

The light source comprises at least one beam positioning means for illuminating at least one spot on the rim of cornea at a slanted angle with the cornea guiding the light from the illuminated spot to the largely full rim of the cornea thereby illuminating the rim by light emitted by scattering of light inside the eye by opaque tissue of the eye at the rim of the cornea. The apparatus can comprise a single light source to illuminate a single spot on the rim of cornea, a spot close to the limbus of the eye. Alternatively, the apparatus can comprise at least one light source to illuminate at least one spot on the sclera without using the cornea as a waveguide.

The camera can, preferably, be fitted with a telecentric lens to provide an image magnification with the degree of magnification independent from the distance of the eye from the objective of the telecentric lens. telecentric lens allows for digital sensor pixel count on the image and thus without aid of external calibration aids such as a Holliday day disc or a calibration bar by direct post processing digital means from the digital image.

The apparatus comprises at least one computer programmed to calculate the diameter of at least one anatomical structure of the eye based on the diameter of the rim of the iris with the anatomical structure being the sulcus of the eye, or, alternatively, the ciliary mass of the eye, or alternatively, the iris of the eye, or, alternatively, any anatomical structure of the eye, or, alternatively, evaluate prior implants in the eye, for example an intraocular lens.

The method for imaging the accommodation structure of the eye including, for example, the ciliary mass and/or the sulcus, pigment layer lining the sulcus, and/or the iris with the can include, but not restricted hereto, positioning the eye along the optical axis of the apparatus, and, positioning the light source at such an angle that the contrast between the by opaque tissue of the eye at the limbus area other than the transparent cornea is maximized followed by obtaining at least one image of the eye by digital camera, and, post-processing of the image to maximize resolution of the rim of the iris followed by calculation of the diameter of the iris at at least one rotational angle, and, calculate or directly measure the diameter of the sulcus and/or ciliary mass and/or any other anatomical component of the eye and/or any other component in the eye.

The diameter of the iris and or any other component of the eye can be illuminated by hyperspectral illumination or, alternatively, the image can be manipulated by hyperspectral post processing to the same effect so the different tissues are differently accentuated in multiple post processed images The illumination can also be accomplished by backlighting of the accommodative structure by illumination of the sclera, without using the cornea as a light guide, which sclera based illumination requires significantly higher light amplitudes to a degree that such illumination does not become uncomfortable, or worse, harmful, to the patient of which the eye is investigated.

The diameter of the sulcus and/or ciliary mass and/or and/or iris and/or any other anatomical component of the eye based on the diameter of the iris, for example the diameter of components of the sulcus including the sulcus-root and/or the diameter of the ciliary mass.

The apparatus can include a second light source, for example a ringlight around the objective of the telecentric lens, with the second light source providing images by frontal illumination to also provide for a general overview of the eye. Note that the second light source can include hyperspectral illumination to accentuate different anatomical structures by different light wavelengths, light frequencies, within the range of UV light to deep infrared light so that different tissues in the eye can be accentuated as well as, for example, an artificial intraocular lens, by, for example, deep blue or ultraviolet light because such intraocular lenses generally comprise blue/UV light filtering chemicals.

The method can include mechanical and/or digital automation of at least one of the steps, for example, identification of accommodative structures by digital image recognition which recognition can be, over time, optimized by artificial intelligence computer learning procedures.

So, in summary, this document discloses an apparatus for imaging and measuring the accommodation structure of the eye, including the iris, ciliary mass and the sulcus, comprising at least one light source for illuminating the eye and, at least one digital camera comprising at least one optical lens for providing at least one digital image with the camera coupled to at least one computer for post-processing the digital image and presenting the digital image on a digital screen with the light source comprises at least one beam positioning means for illuminating at least one spot on the rim of cornea at a slanted angle with the cornea guiding the light from the illuminated spot to the largely full rim of the cornea thereby illuminating the rim by light emitted by scattering of light inside the eye by opaque tissue of the eye at the rim of the cornea, and, with the optical lens is a telecentric lens providing an image magnification with the degree of magnification independent from the distance of the eye from the objective of the telecentric lens. The apparatus can comprises a single light source to illuminate a single spot on the rim of cornea with a light source which cvan comprise at least one shape adjustment component to provide adjustability of the shape of the illumination spot, for example, a shifting wedge shaped mask. The computer can be programmed to establish the diameter of anatomical structures of the eye based on the diameter of the rim of the iris and/or other anatomical structures, including the sulcus of the eye and/or the ciliary mass of the eye. A method for imaging the accommodative structure of the eye including the ciliary mass, the iris and the sulcus, van comprise the steps of positioning the eye along an optical axis of a measuring apparatus, preferably according to any of the foregoing Claims, positioning and adjusting an illumination spot, preferably at such an angle that the contrast between the by opaque tissue of the eye and the transparent cornea is maximized, with the illumination spot illuminating the accommodative structure, obtaining at least one digital image of the illuminated accommodative structure, and establishing the diameter of the rim of the iris and/or sulcus and/or ciliary mass and/or any other anatomical component of the eye based on the digital image. Establishment of the diameter of the anatomical component of the eye includes a digital sensor pixel count. Post-processing the digital image can maximize resolution of the rim of the iris and/or any other anatomical structure followed by establishment of the diameter of any anatomical structure at at least one angle. Also, the illumination can provide by hyperspectral illumination and/or wherein the post processing can include hyperspectral post processing.

The invention claimed is:

1. An apparatus for imaging and measuring an accommodation structure of an eye, the accommodation structure including an iris, a ciliary mass, and a sulcus of the eve, the apparatus comprising:

at least one light source for illuminating the eye, and at least one digital camera comprising at least one optical lens for providing at least one digital image with the at least one digital camera, the at least one digital camera being coupled to at least one computer for post-processing the at least one digital image and presenting the at least one digital image on a digital screen, wherein the at least one light source comprises at least one beam positioning means for illuminating at least one spot on a rim of a cornea at a slanted angle with the cornea guiding the light from the illuminated at least one spot to largely fill an entirety of the rim of the cornea thereby illuminating the rim by light emitted by scattering of light inside the eye by opaque tissue of the eye at the rim of the cornea, wherein the at least one optical lens of the at least one digital camera is a telecentric lens providing an image magnification with a degree of magnification independent from a distance of the eye from an objective of the telecentric lens, and wherein the computer is programmed to calculate a diameter of the sulcus of the eye or the ciliary mass of the eve based on a diameter of the rim of the cornea illuminated by the light from the at least one light source measured by analysis of the at least one digital image.

2. The apparatus according to claim 1, wherein the apparatus comprises a single light source to illuminate a single spot on the rim of cornea.

3. The apparatus according to claim 2, wherein the at least one light source comprises at least one shape adjustment component to provide adjustability of the shape of the illuminated at least one spot.

4. A method for imaging an accommodative structure of an eye, the accommodative structure including a ciliary mass, an iris, and a sulcus of the eye, the method comprising:

a. positioning the eye along an optical axis of the apparatus for imaging and measuring the accommodation structure of the eye according to claim 1,
b. positioning and adjusting the illuminated at least one spot, preferably at such an angle that the contrast between the opaque tissue of the eye and the transparent cornea is maximized, wherein the illuminated at least one spot illuminates the accommodation structure;
c. obtaining at least one digital image of the illuminated accommodation structure, and
d. establishing the diameter of the rim of the iris and/or sulcus and/or ciliary mass and/or any other anatomical component of the eye based on measurements of the rim of the cornea determined by analysis of the at least one digital image.

5. The method according to claim 4, wherein establishing the diameter of the rim of the cornea of the eye includes a digital sensor pixel count.

6. The method according to claim 4, further comprising a step of post-processing the at least one digital image by at least one of digital merging of multiple images or processing by digital image-enhancing processing to maximize resolution of any anatomical component of the eye followed by establishment of the diameter of the rim of the cornea at an at least one angle.

7. The method of claim 6, wherein the at least one light source comprises a wide range broadband white light at any angle, and wherein the post-processing comprises, with the computer, providing processing by digital image-enhancing processing to increase resolution.

8. The method according to claim 4, wherein the illumination is provided by hyperspectral illumination.

9. The method according to claim 4, wherein the post processing includes hyperspectral post processing.

* * * * *